(12) United States Patent
Maiorino et al.

(10) Patent No.: US 8,222,564 B2
(45) Date of Patent: Jul. 17, 2012

(54) METHODS OF ALTERING SURGICAL FIBER

(75) Inventors: Nicholas Maiorino, Branford, CT (US); Michael Primavera, Orange, CT (US); Matthew D. Cohen, Berlin, CT (US)

(73) Assignee: Tyco Healthcare Group, LP, Mansfield, MA (US)

( * ) Notice: Subject to any disclaimer, the term of this patent is extended or adjusted under 35 U.S.C. 154(b) by 811 days.

(21) Appl. No.: 12/352,956

(22) Filed: Jan. 13, 2009

(65) Prior Publication Data

US 2009/0200487 A1 Aug. 13, 2009

Related U.S. Application Data

(60) Provisional application No. 61/028,205, filed on Feb. 13, 2008.

(51) Int. Cl.
*A61B 17/04* (2006.01)
(52) U.S. Cl. ............... 219/121.69; 606/224; 250/492.1
(58) Field of Classification Search ............ 219/121.68, 219/121.69, 121.85, 121.7, 121.71; 606/224, 606/226, 227, 228, 222, 223; 29/282, 517; 72/409.19; 250/492.1
See application file for complete search history.

(56) References Cited

U.S. PATENT DOCUMENTS

| | | | |
|---|---|---|---|
| 3,038,475 A * | 6/1962 | Orcutt ........................ 606/223 |
| 3,408,773 A | 11/1968 | Cole et al. | |
| 3,910,282 A | 10/1975 | Messer et al. | |
| 3,918,455 A | 11/1975 | Coplan | |
| 3,926,194 A | 12/1975 | Greenberg et al. | |
| 3,943,933 A | 3/1976 | Gertzman | |
| 4,268,954 A * | 5/1981 | Sease et al. ..................... 29/620 |
| 4,761,535 A * | 8/1988 | Lawson ................... 219/121.68 |
| 5,007,922 A | 4/1991 | Chen et al. | |
| 5,017,423 A | 5/1991 | Bossmann et al. | |
| 5,041,128 A | 8/1991 | Korthoff | |
| 5,059,212 A | 10/1991 | Korthoff | |
| 5,089,011 A | 2/1992 | Korthoff | |
| 5,139,514 A | 8/1992 | Korthoff | |
| 5,156,615 A | 10/1992 | Korthoff | |
| 5,269,056 A * | 12/1993 | Yang et al. ...................... 29/879 |
| 5,269,808 A | 12/1993 | Proto et al. | |
| 5,280,674 A | 1/1994 | Granger et al. | |
| 5,358,498 A | 10/1994 | Shave | |
| 5,383,902 A | 1/1995 | Carpentiere et al. | |
| 5,403,345 A | 4/1995 | Spingler | |
| 5,430,816 A * | 7/1995 | Furuya et al. ................... 385/33 |
| 5,479,980 A | 1/1996 | Spingler | |
| 5,507,798 A | 4/1996 | Colligan et al. | |
| 5,568,746 A | 10/1996 | Colligan et al. | |
| 5,693,071 A | 12/1997 | Gorecki et al. | |

(Continued)

FOREIGN PATENT DOCUMENTS

EP 0501225 9/1992

(Continued)

OTHER PUBLICATIONS

European Search Report, Application No. EP 09250337 dated May 21, 2010.

*Primary Examiner* — Samuel M Heinrich

(57) ABSTRACT

The present disclosure relates to methods of altering a surgical fiber by irradiating the surgical fiber with an energy beam such that material is removed therefrom.

18 Claims, 6 Drawing Sheets

U.S. PATENT DOCUMENTS

| | | |
|---|---|---|
| 5,747,770 A | 5/1998 | Bogart |
| 5,792,181 A | 8/1998 | Haase et al. |
| 5,865,836 A | 2/1999 | Miller |
| 5,915,751 A * | 6/1999 | Esteves et al. ............ 29/783 |
| 5,931,855 A * | 8/1999 | Buncke ............ 606/228 |
| 5,941,899 A | 8/1999 | Granger et al. |
| 5,968,076 A | 10/1999 | Granger et al. |
| 5,975,876 A | 11/1999 | Haase et al. |
| 6,001,121 A | 12/1999 | Haase et al. |
| 6,024,757 A | 2/2000 | Haase et al. |
| 6,319,445 B1 | 11/2001 | Haase et al. |
| 6,481,648 B1 * | 11/2002 | Zimmermann ............ 239/690 |
| 2004/0088003 A1 * | 5/2004 | Leung et al. ............ 606/228 |

FOREIGN PATENT DOCUMENTS

| | | |
|---|---|---|
| EP | 0428110 | 7/2010 |
| FR | 2231797 | 12/1974 |
| JP | 08182142 A * | 7/1996 |

* cited by examiner

METHODS OF ALTERING SURGICAL FIBER

CROSS-REFERENCE TO RELATED APPLICATIONS

This application claims the benefit of and priority to U.S. Provisional Patent Application No. 61/028,205, filed Feb. 13, 2008, the entire disclosure of which is incorporated by reference herein.

BACKGROUND

1. Technical Field

The present disclosure relates to a method of altering a surgical fiber. In particular, the present disclosure relates to methods of removing at least a portion of the surgical fiber to facilitate the coupling thereof with a surgical needle.

2. Background of the Related Art

Surgical fibers have many uses in contemporary medical practice. These include joining skin, internal organs, blood vessels, and other tissues of the body together after they have been severed by injury or surgery. To serve this end, the surgical fiber is passed through the tissue to be joined using a surgical needle or other such surgical device. To facilitate coupling of the surgical fiber with the surgical needle, it is often necessary to alter the surgical fiber.

Conventionally, the surgical fiber is altered through the use of mechanical machining methods, such as cutting, grinding, and/or milling. However, mechanical machining methods are generally slow, and over time, the devices employed in these methods wear, creating variations in accuracy and precision of the finished product.

Accordingly, a need exists in the art for a method of altering surgical fibers that addresses the deficiencies of mechanical machining methods.

SUMMARY

In one aspect of the present disclosure, a method of altering a surgical fiber is disclosed. The method comprises the steps of providing the surgical fiber, at least a portion of which defines a first axis, providing an irradiating device for emitting at least one beam, and directing the at least one beam at the surgical fiber for a time and with an intensity sufficient to remove material therefrom such that a reduced portion is formed that is configured and dimensioned for coupling with a surgical needle.

In one embodiment, the irradiating device emits the at least one beam along a second axis that extends in transverse relation to the first axis. It is further contemplated that in one embodiment, the method may further comprise the step of providing a curved reflector for redirecting the at least one beam such that it is simultaneously or sequentially incident upon the surgical fiber from a plurality of angles.

The step of providing the surgical fiber may comprise providing a holder for releasably engaging the surgical fiber during the irradiation thereof. The holder may be fixed with respect to the curved reflector. The irradiating device may be fixed with respect to the holder. The holder may be configured to rotate the surgical fiber about the first axis. The holder and the curved reflector may be configured for relative movement therebetween. The irradiating device and the holder may be configured for relative movement therebetween, or the irradiating device may be configured to move along the first axis.

The at least one beam may be directed at the surgical fiber such that the reduced portion defines a substantially non-uniform topography to facilitate anchoring of the reduced portion with the surgical needle.

In an alternate aspect of the present disclosure, the step of directing the at least one beam at the surgical fiber may also include directing the at least one beam substantially along the first axis such that the material is removed from an internal region of the surgical fiber to thereby form a cavity. Subsequent thereto, a force may be applied to the surgical fiber to thereby reduce its initial outer dimension.

In yet another aspect of the present disclosure, a method of altering a surgical fiber to facilitate the coupling thereof with the surgical needle is disclosed. The method comprises the steps of providing a surgical fiber, at least a portion of which extends along a first axis, providing a plurality of irradiating devices for emitting at least one beam, and directing the at least one beam at said surgical fiber for a time and with an intensity sufficient to remove material therefrom In one embodiment, the irradiating devices are oriented in spaced apart relation along the first axis defined by the surgical fiber.

The plurality of irradiating devices and the holder may be configured for relative movement therebetween. The plurality of irradiating devices may be fixed in relation to the holder. The holder may be configured to rotate the surgical fiber about the first axis, or the plurality of irradiating devices may be configured to move along the first axis.

These and other features of the methods disclosed herein will become more readily apparent to those skilled in the art from the following detailed description of various embodiments of the present disclosure.

BRIEF DESCRIPTION OF THE DRAWINGS

Various embodiments of the present disclosure are described hereinbelow with references to the drawings, wherein.

DETAILED DESCRIPTION OF THE EMBODIMENTS

Figure 1:
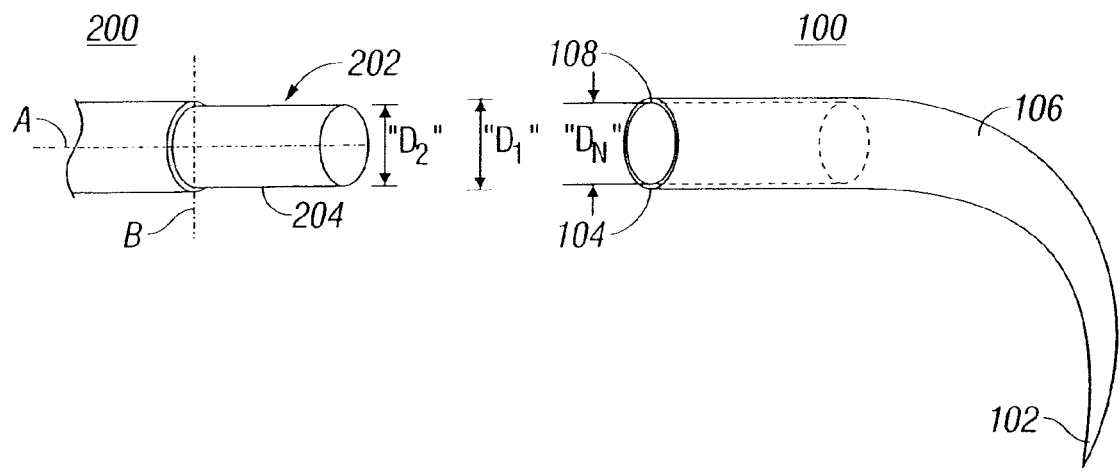
FIG. 1 is a perspective view of an exemplary surgical fiber removed from a surgical needle.

In the drawings and in the description which follows, in which like references numerals identify similar or identical elements, the term "surgical fiber" should be understood to refer to any surgical grade suture, filament, tape, or the like suitable for the intended purpose of joining severed tissue.

With reference now to FIG. 1, an exemplary surgical needle 100 and a surgical fiber 200 are illustrated. Surgical needle 100 may be formed of any suitable biocompatible material, including but not limited to stainless steel, and includes respective first and second ends 102, 104 with a shaft 106 extending therebetween that may be curved, as shown, or substantially straight. Further details regarding surgical needle 100, as well as methods of altering surgical needles and attaching surgical needles to surgical fibers, are disclosed in U.S. Pat. Nos. 5,383,902, 5,479,980, 5,507,798, 5,568,746, 5,693,071, 5,747,770, 5,865,836, 5,941,899, and 5,968,076, the entire contents of which are incorporated by reference herein.

First end 102 may exhibit any configuration suitable for penetration of tissue, and may be substantially incisive, as shown, or substantially blunt.

Second end 104 includes receiving structure 108. Receiving structure 108 defines an internal dimension "$D_N$" sized to receive a first end 202 of surgical fiber 200, and corresponds in configuration thereto, such that surgical fiber 200 and surgical needle 100 may be coupled together.

Surgical fiber 200 may be formed of any suitable biocompatible material, including but not being limited to polypropylene, polyester, nylon, or stainless steel, and extends at least partially along an axis "A". Initially, in an unaltered condition, surgical fiber 200 defines an outer dimension "$D_1$" measured along an axis "B" that is orthogonal in relation to the axis "A" along which surgical fiber 200 extends. The initial outer dimension "$D_1$" of surgical fiber 200 is substantially larger than the internal dimension "$D_N$" of the receiving structure 108, thereby prohibiting the coupling of surgical fiber 200 and surgical needle 100. However, the initial outer dimension "$D_1$" of surgical fiber 200 may be reduced, through the process discussed herein below, such that a reduced portion 204 is defined. The reduced portion 204 defines a second outer dimension "$D_2$" that facilitates the insertion of first end 202 of surgical fiber 200 into the receiving structure 108 of surgical needle 100 such that surgical fiber 200 and surgical needle 100 may be coupled together by coining, crimping, or through the use of adhesives, as is known in the art.

Figure 2A:
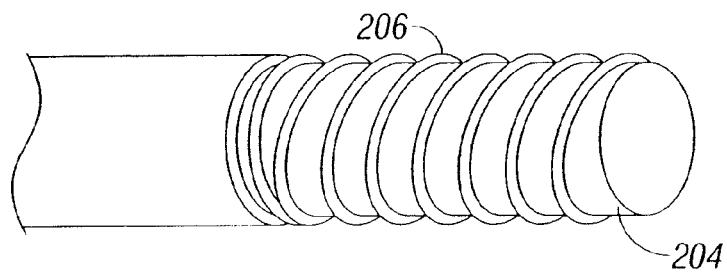
FIGS. 2A-2C are side perspective views of alternate embodiments of the surgical fiber of FIG. 1.
Figure 2B:
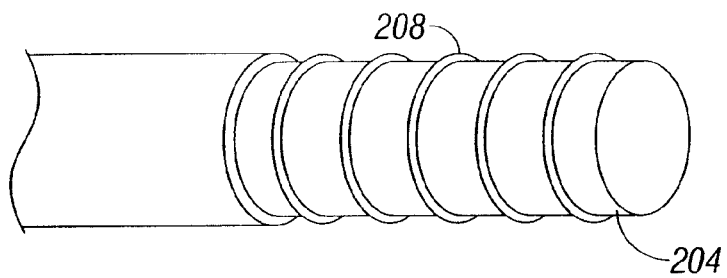
Figure 2C:
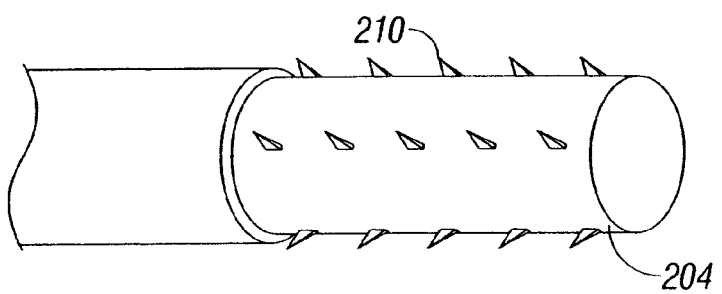

As illustrated in FIG. 1, the reduced portion 204 may define a substantially uniform topography. Alternatively, as seen in FIGS. 2A-2C, the reduced portion 204 may define a substantially non-uniform topography, e.g., inclusive of threads 206, ribs 208, or barbs 210 to assist in the anchoring of the reduced portion 204 within the receiving structure 108.

Figure 3A:
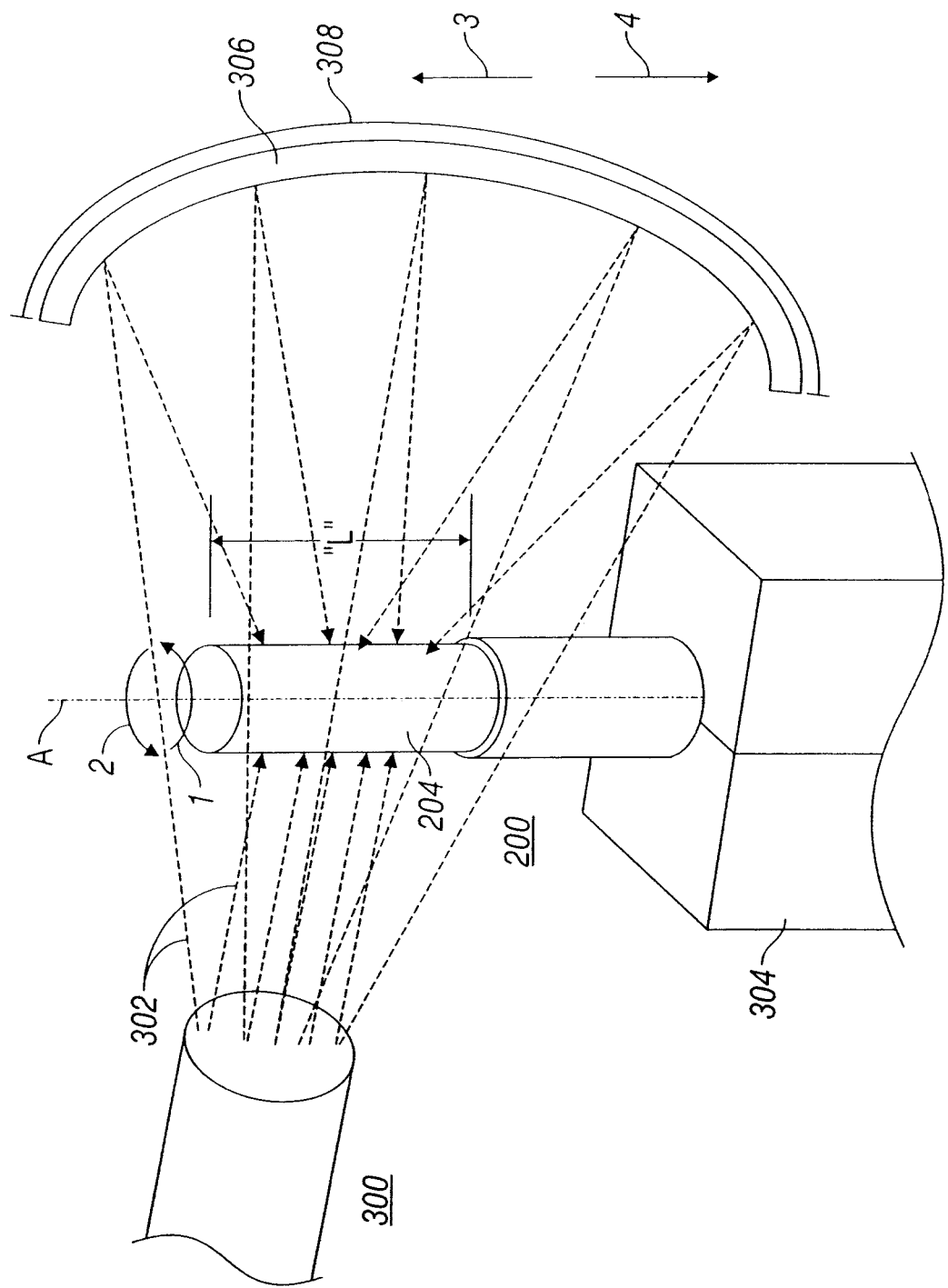
FIG. 3A is a perspective view of an irradiating device, a curved reflector, and a holder for use in a method of altering the surgical fiber of FIG. 1.
Figure 3B:
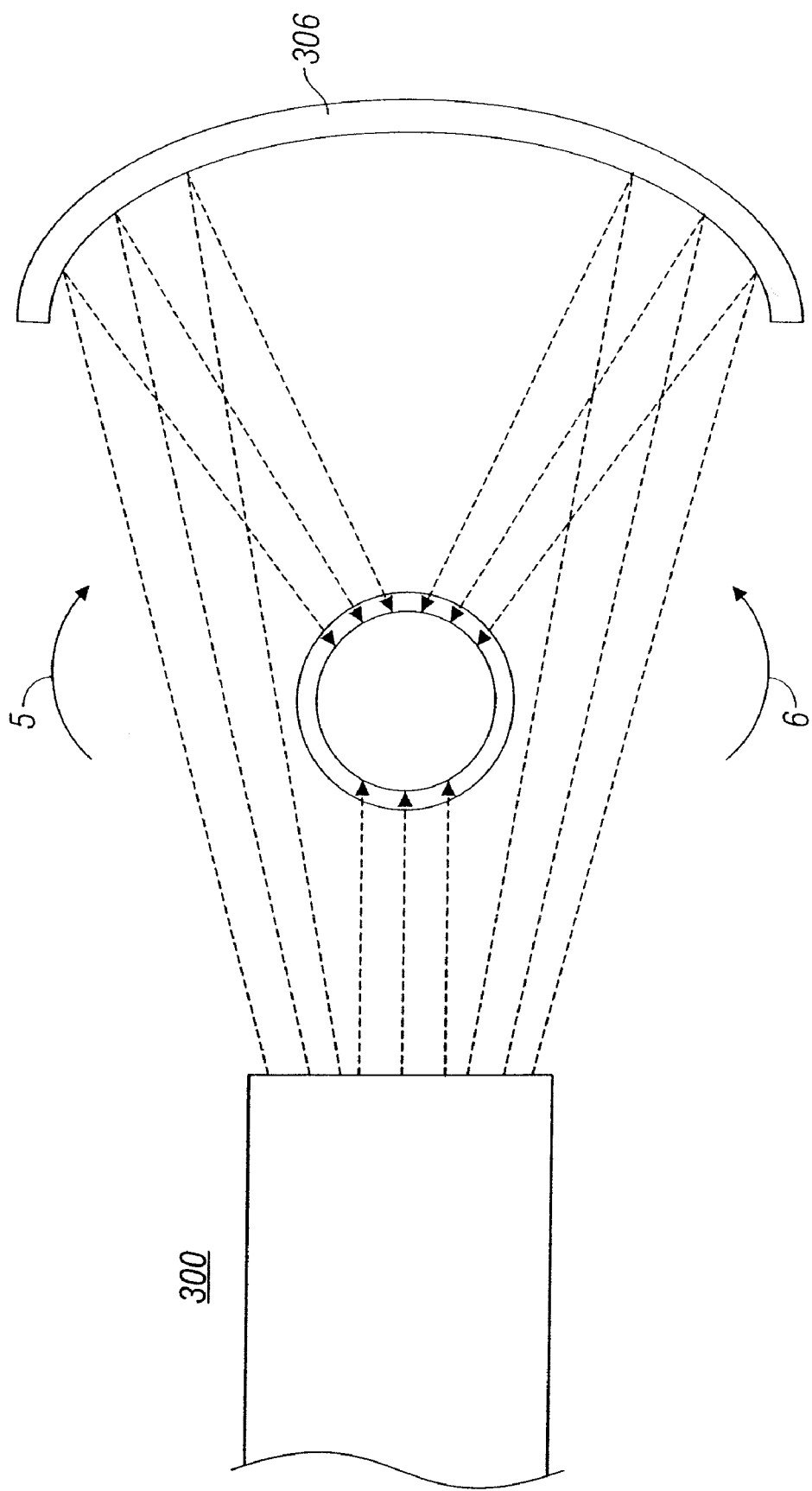
FIG. 3B is a top view of the irradiating device, the curved reflector, and the holder of FIG. 3A.

Referring now to FIGS. 1 and 3A-3B, a method of reducing the initial outer dimension "$D_1$" of surgical fiber 200 will be discussed. The disclosed method employs an irradiating device 300 to effectuate localized ablation of the material comprising surgical fiber 200. Irradiating device 300 generates and emits at least one beam 302 that is incident upon surgical fiber 200 to cause a reduction in its initial outer dimension "$D_1$" and thereby define the reduced portion 204 discussed above. While the present disclosure contemplates the use of an irradiating device 300 that emits a laser beam, any irradiating device 300 adapted to emit an energy beam capable of accomplishing the functional aspects of the presently disclosed method may be employed.

Various parameters of beam 302, including but not being limited to the scan rate, peak power, pulse repetition rate, spot size, energy per pulse, pulse width, and wavelength, can manipulated dependent upon the material constituting surgical fiber 200 so as to control the removal of material from the suture. For example, the laser removal of polymeric materials is often performed with lasers that generate pulsed beams at wavelengths of 248 nm, 193 nm, or less, as shorter wavelengths and pulses reduce any excess heat that may be generated which could otherwise damage the workpiece, i.e. the surgical fiber 200.

During alteration, the surgical fiber 200 is maintained within a holder 304 configured for the releasable engagement thereof. A portion of the beams 302 emitted by irradiating device 300 are directly incident upon surgical fiber 200, whereas a remaining portion of beam 302 are directed past surgical fiber 200. In one embodiment, the portion of beams 302 directed past surgical fiber 200 are redirected by a curved reflector 306 such that the beams 302 emitted by irradiating device 300 are incident upon surgical fiber 200 from 3600, thereby facilitating the uniform irradiation of surgical fiber 200. While FIGS. 3A and 3B illustrate beams 302 which are emitted from irradiating device 300 along axis "B", which is orthogonal to the axis "A" defined by surgical fiber 200, irradiating device 300 may be configured so as to emit beams 302 along any suitable transverse axis which intersects axis "A", or along axis "A" itself. Curved reflector 306 may define any arc length 308 suitable for this intended purpose. Beams 302 may be directed simultaneously or sequentially at surgical fiber 200.

The curved reflector 306 and the irradiating device 300 may each remain stationary during the irradiation of surgical fiber 200, in which instance, the holder 304 may be adapted to rotate the surgical fiber 200, in the direction indicated by arrows 1 and 2, about the axis "A" defined by thereby to further ensure uniform irradiation. Holder 304 may also be adapted to translate along the axis "A" in the direction of arrows 3 and 4 to selectively define an axial dimension "L" of the reduced portion 204. In an alternate embodiment, the holder 304 may remain stationary, and irradiating device 300 and reflector 306 may be configured to effect relative movement with respect to holder 304 to assure uniform irradiation of surgical fiber 200. As an example, either or both of the irradiating device 300 and the reflector 306 may be configured to revolve about the holder 304 in the directions indicated by arrows 5 and 6, as seen in FIG. 3B. The irradiating device 300 and the reflector 306 may also be configured to translate along the axis "A" in the direction of arrows 3 and 4 to thereby selectively define the axial dimension "L" of the reduced portion 204.

Figure 4A:
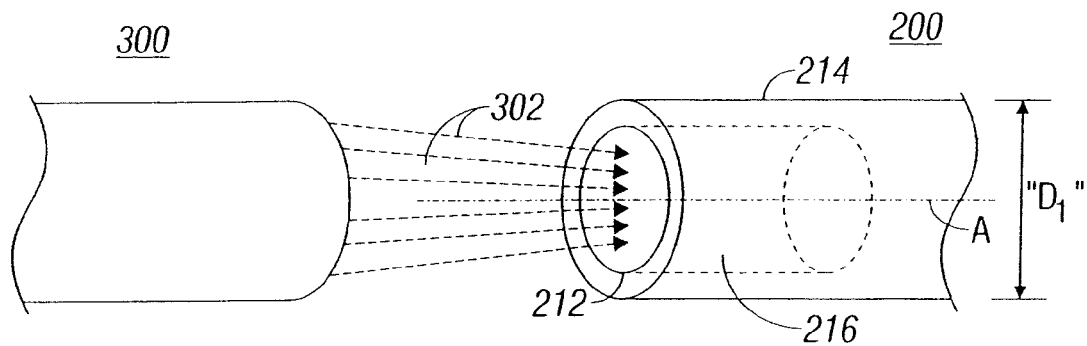
FIG. 4A is a side perspective view of the irradiating device for use in an alternate method of altering the surgical fiber of FIG. 1.
Figure 4B:
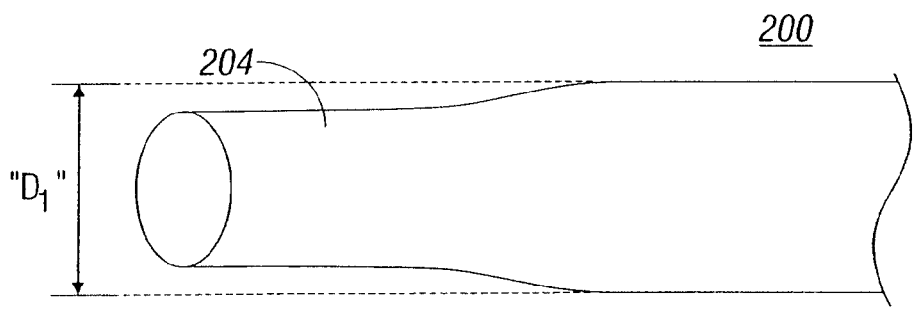
FIG. 4B is a side perspective view of the surgical fiber of FIG. 4A subsequent to alteration.
Figure 4C:
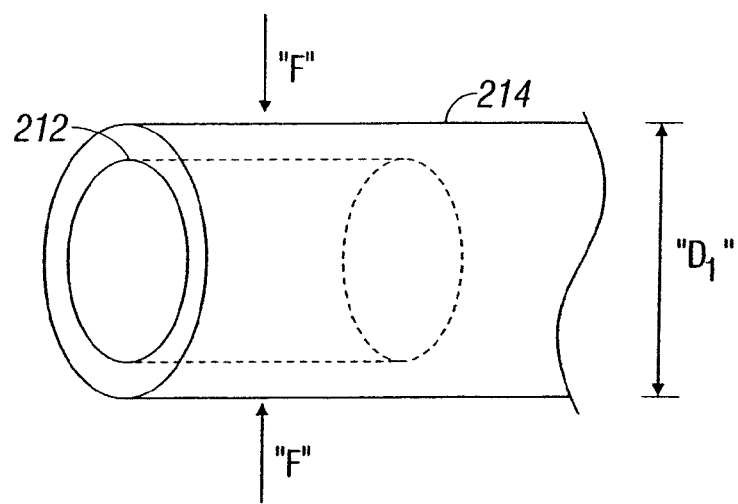
FIG. 4C is a side perspective view of the surgical fiber of FIG. 4B in which an outer dimension thereof is reduced through the application of an external force subsequent to alteration.

With reference now to FIGS. 4A-4B, in an alternate aspect of the present disclosure, the beams 302 generated by irradiating device 300 may be incident upon surgical fiber 200 substantially along the axis "A" defined thereby, as discussed previously. Upon contacting surgical fiber 200, the beams 302 will remove material from an internal region 212 thereof defined beneath an outer surface 214 of surgical fiber 200 and form a cavity 216. The beams 302 may be of sufficient intensity, and may be incident upon internal region 212 for a sufficient amount of time, such that upon the removal of material from internal region 212, the outer surface 214 of surgical fiber 200 will collapse inwardly upon cavity 216, thereby causing a reduction in the initial outer dimension "$D_1$" of surgical fiber 200 and defining the reduced portion 204 discussed above with respect to FIG. 1. However, the present disclosure also contemplates that the outer surface 214 of surgical fiber 200 may not collapse inwardly upon the removal of material from internal region 212, in which event the initial outer dimension "$D_1$" of surgical fiber 200 will be reduced, and the reduced portion 204 defined (FIG. 4B), through the application of an external force "F" to the outer surface 214 of surgical fiber 200, as seen in FIG. 4C. Force "F" may be created in any suitable manner, including but not limited to the employ of a clamp, crimping, or coining apparatus (not shown).

Figure 4D:
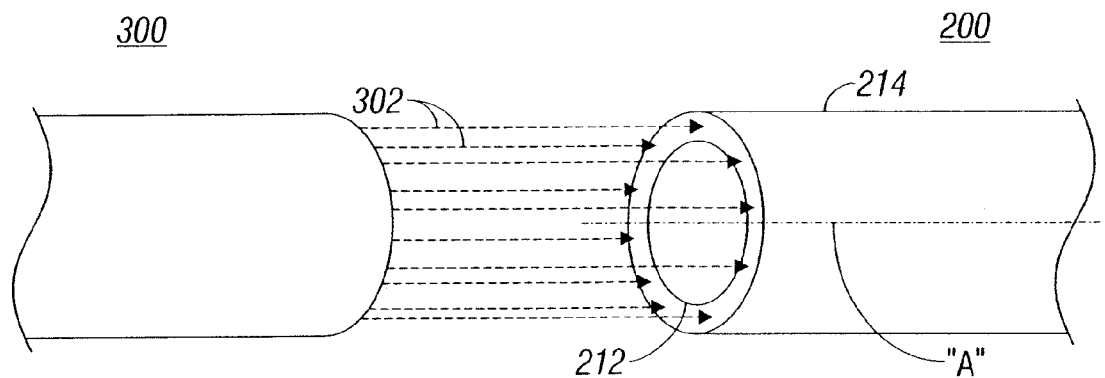
FIG. 4D is a side perspective view of the irradiating device for use in another method of altering the surgical fiber of FIG. 1.
Figure 4E:
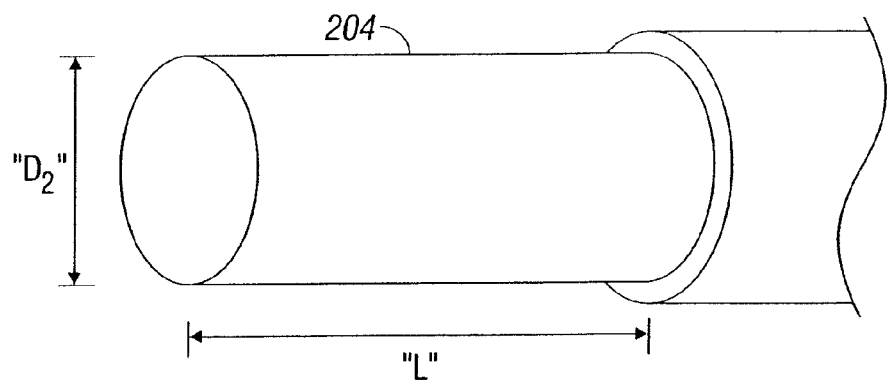
FIG. 4E is a side perspective view of the surgical fiber of FIG. 4D subsequent to alteration.

Alternatively, rather than directing the beams 302 at the internal region 212 of surgical fiber 200, the beams 302 may be directed to remove material from the outer surface 214 thereof, as seen in FIG. 4D. To regulate the amount of material removed from outer surface 214, the beams 302 may be directed progressively inward, i.e. towards axis "A", during the irradiation period. Moreover, by varying the irradiation period and/or one or more parameters of the irradiating device 300 or beams 302, e.g. the scan rate, peak power, pulse repetition rate, spot size, energy per pulse, pulse width, or wavelength, the amount of material removed from surgical fiber 200 may be further controlled, thereby permitting the formation of a reduced portion 204 (FIG. 4E) defining a particular or desired outer dimension "$D_2$" and/or axial dimension "L".

Figure 5:
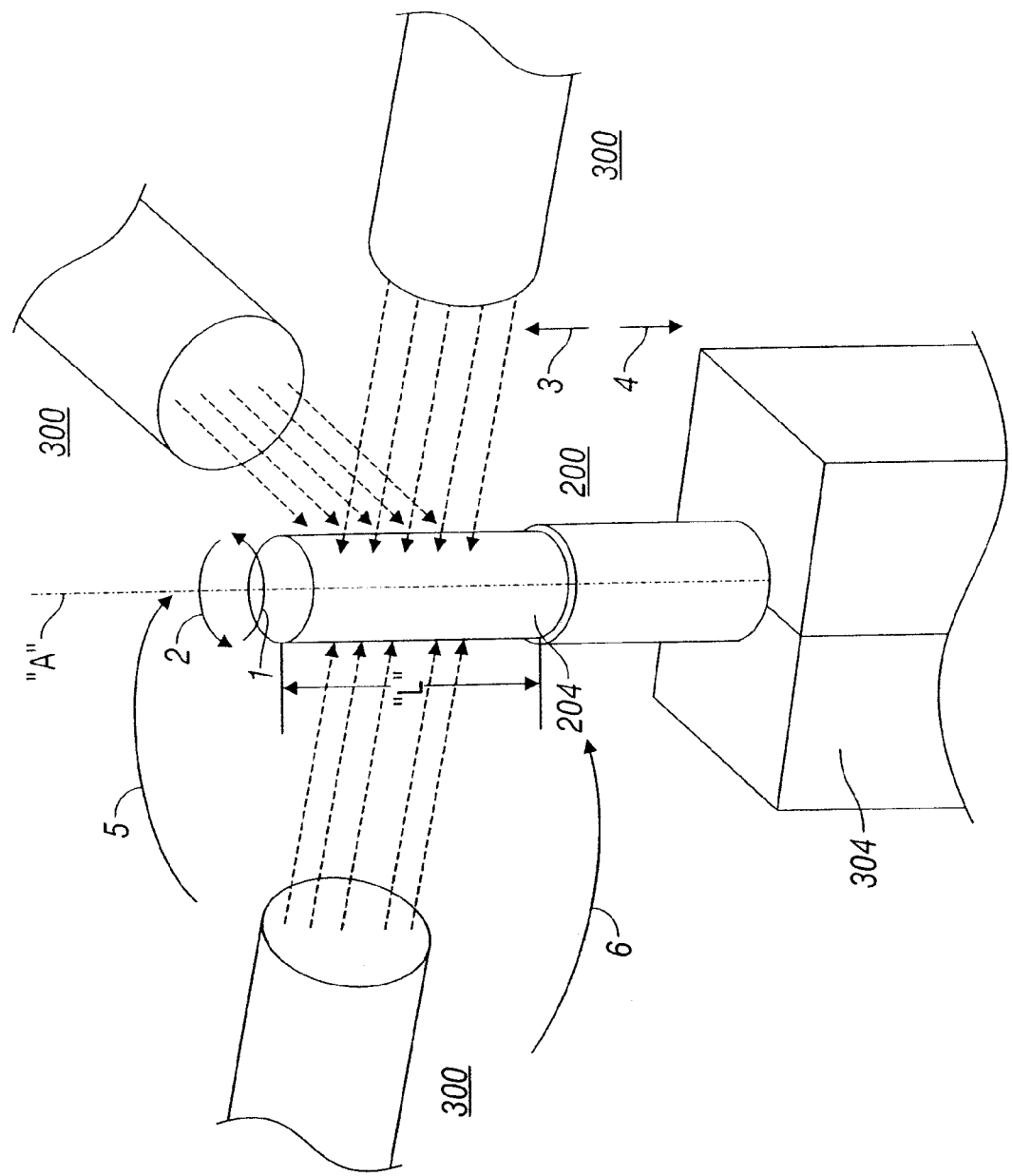
FIG. 5 is a perspective view of a plurality of irradiating devices and a holder for use in yet another method of altering the surgical fiber of FIG. 1.

With reference now to FIGS. 5A-5B, in still another aspect of the present disclosure, a method of altering surgical fiber 200, e.g. reducing the initial outer dimension "$D_1$" thereof, is disclosed which employs a plurality of irradiating devices 300. Any suitable number of irradiating devices 300 facilitating the even irradiation of the surgical fiber 200 may be utilized. The irradiating devices 300 are oriented about holder 304 and may be spaced apart from one another along the axis "A" defined by the surgical fiber 200.

In one embodiment, the holder 304 may be configured to rotate the surgical fiber 200 about the axis "A" in the direction indicated by arrows 1 and 2. Additionally, or alternatively, the holder 304 may be adapted to translate along the longitudinal axis "A" in the direction indicated arrows 3 and 4 to thereby selectively define the axial dimension "L" of the reduced portion 204, as discussed above with respect to the embodiment of FIGS. 3A-3B. In an alternate embodiment, the irradiating devices 300 may be configured to effect relative movement with respect to the holder 304, e.g., the irradiating devices 300 may be configured to revolve about the holder 304 in the directions indicated by arrows 5 and 6. In this embodiment, the plurality of irradiating devices 300 may also be configured to translate along the axis "A" in the direction indicated by arrows 2 and 3.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A method of altering a surgical fiber, comprising the steps of:
   providing a surgical fiber, at least a portion of the surgical fiber defining a first axis;
   providing an irradiating device for emitting at least one beam;
   directing the at least one beam at the surgical fiber for a time and with an intensity sufficient to remove material therefrom such that a reduced portion is formed configured and dimensioned for coupling with a surgical needle, wherein the step of directing the at least one beam at the surgical fiber includes directing the at least one beam substantially along the first axis such that the material is removed from an internal region of the surgical fiber to thereby form a cavity; and
   applying a force to the surgical fiber subsequent to the creation of the cavity to thereby reduce an initial outer dimension of the surgical fiber.

2. The method of claim 1, further comprising the step of providing a curved reflector for redirecting the at least one beam such that the at least one beam is incident upon the surgical fiber from a plurality of angles.

3. The method of claim 2, wherein the step of providing a surgical fiber comprises providing a holder for releasably engaging the surgical fiber during the irradiation thereof.

4. The method of claim 3, wherein the step of providing a surgical fiber comprises providing the holder such that the holder is fixed with respect to the curved reflector.

5. The method of claim 4, wherein the step of providing an irradiating device comprises providing the irradiating device such that the irradiating device is fixed with respect to the holder.

6. The method of claim 5, wherein the step of providing a surgical fiber comprises providing the holder such that the holder is configured to rotate the surgical fiber about the first axis.

7. The method of claim 3, wherein the steps of providing a surgical fiber and providing a curved reflector respectively comprise providing the holder and providing the curved reflector such that the holder and the curved reflector are configured for relative movement therebetween.

8. The method of claim 7, wherein the steps of providing at least one irradiating device and providing a surgical fiber respectively comprise providing the irradiating device and providing the holder such that the irradiating device and the holder are configured for relative movement therebetween.

9. The method of claim 8, wherein the step of proving an irradiating device comprises providing the irradiating device such that the irradiating device is adapted to emit the at least one beam along a second axis extending in transverse relation to the first axis.

10. The method of claim 9, wherein the step of proving an irradiating device comprises providing the irradiating device such that the irradiating device is configured to move along the first axis.

11. The method of claim 1, wherein the step of directing the at least one beam at the surgical fiber includes directing the at least one beam such that the reduced portion defines a substantially non-uniform topography to facilitate anchoring of the reduced portion with the surgical needle.

12. A method of altering a surgical fiber to facilitate the coupling thereof with a surgical needle, comprising the steps of:
   providing a surgical fiber, wherein at least a portion of the surgical fiber extends along a first axis;
   providing a plurality of irradiating devices for emitting at least one beam;
   directing the at least one beam at said surgical fiber for a time and with an intensity sufficient to remove material therefrom, wherein the step of directing the at least one beam at the surgical fiber includes directing the at least one beam substantially along the first axis such that the material is removed from an internal region of the surgical fiber to thereby form a cavity; and
   applying a force to the surgical fiber subsequent to the creation of the cavity to thereby reduce an initial outer dimension of the surgical fiber.

13. The method of claim 12, wherein the step of providing a plurality of irradiating devices comprises providing the plurality of irradiating devices such that the irradiating devices are oriented in spaced apart relation along the first axis.

14. The method of claim 12, wherein the step of providing a surgical fiber comprises providing a holder to releasably engage the surgical fiber during the irradiation thereof.

15. The method of claim 14, wherein the steps of providing a plurality of irradiating devices and providing a surgical fiber respectively comprise providing the plurality of irradiating devices and providing the holder such that the irradiating devices and the holder are configured for relative movement therebetween.

16. The method of claim 14, wherein the step of providing a plurality of irradiating devices comprises providing the plurality of irradiating devices such that the irradiating devices are fixed in relation to the holder.

17. The method of claim 16, wherein the step of providing a surgical fiber comprises providing the holder such that the holder is configured to rotate the surgical fiber about the first axis.

18. The method of claim 17, wherein the step of proving a plurality of irradiating devices comprises providing the plurality of irradiating devices such that the irradiating devices are configured to move along the first axis.

* * * * *